United States Patent [19]
Ruszkay et al.

[11] Patent Number: 5,710,316
[45] Date of Patent: Jan. 20, 1998

[54] TRANSESTERIFICATION PROCESS FOR MAKING ALLYL ESTERS OF AROMATIC CARBOXYLIC ACIDS

[75] Inventors: Jude T. Ruszkay, Coatesville; Katherine A. McCarron, Glen Mill, both of Pa.

[73] Assignee: Arco Chemical Technology, L.P., Greenville, Del.

[21] Appl. No.: 757,522

[22] Filed: Nov. 27, 1996

[51] Int. Cl.$^6$ ............................................. C07C 69/76
[52] U.S. Cl. ......................................... 560/95; 560/99
[58] Field of Search ............................ 560/96, 95, 99

[56] References Cited

U.S. PATENT DOCUMENTS

| | | | |
|---|---|---|---|
| 525,093 | 2/1894 | Yoshinobu et al. | |
| 2,218,439 | 11/1940 | Rothrock | 260/78 |
| 2,275,467 | 3/1942 | Pollack et al. | 260/475 |
| 2,405,842 | 8/1946 | Magrane et al. | 260/475 |
| 2,557,639 | 6/1951 | Derr et al. | 260/475 |
| 3,250,801 | 5/1966 | Stange et al. | 260/468 |
| 3,574,705 | 4/1971 | Linden et al. | 260/475 |
| 3,784,578 | 1/1974 | Swodenk | 260/410.9 |
| 4,473,702 | 9/1984 | Seguchi | 560/80 |
| 5,194,324 | 3/1993 | Uchida et al. | |

*Primary Examiner*—Samuel Barts
*Attorney, Agent, or Firm*—Jonathan L. Schuchardt

[57] ABSTRACT

A transesterification process for making allyl esters of aromatic carboxylic acids from the corresponding alkyl esters and allylic alcohols is disclosed. The alkyl ester/allylic alcohol mixture is dried by distillation to less than about 200 ppm water before heating it in the presence of the transesterification catalyst. The resulting allyl ester is obtained rapidly in high yield with a minimal level of catalyst. In addition, product isolation is simple, and color is exceptionally low. The process is particularly valuable for making diallyl phthalate from dialkyl esters of phthalic acid.

13 Claims, No Drawings

TRANSESTERIFICATION PROCESS FOR MAKING ALLYL ESTERS OF AROMATIC CARBOXYLIC ACIDS

FIELD OF THE INVENTION

The invention relates to processes for making allyl esters of aromatic carboxylic acids. In particular, the invention is a transesterification process that is especially valuable for making diallyl esters such as diallyl phthalate.

BACKGROUND OF THE INVENTION

Allyl esters of carboxylic acids, especially dicarboxylic acid esters, are valuable chemical intermediates for thermosetting molding plastics. Diallyl phthalate (DAP), one of the most important diesters, gives plastics with excellent solvent and heat resistance, desirable electrical properties, and good dimensional stability.

The most popular synthetic route to diallyl phthalate involves direct esterification. Phthalic anhydride and allyl alcohol react, usually in the presence of an acidic catalyst (e.g., sulfuric acid or an organosulfonic acid), to give diallyl phthalate (see, e.g., U.S. Pat. Nos. 2,405,842 and 2,557, 639). Other methods first convert phthalic anhydride or phthalic acid to disodium phthalate, and then react the disodium salt with allyl chloride to give DAP (see, e.g., U.S. Pat. Nos. 2,275,467 and 3,574,705). Phthalic anhydride also reacts with allyl chloride in the presence of sodium bicarbonate and a quaternary ammonium salt to give DAP in a single step (see U.S. Pat. No. 3,250,801 ).

Transesterification processes for making allyl esters of aromatic dicarboxylic acids are also known. U.S. Pat. No. 2,218,439, for example, teaches to prepare DAP by refluxing a mixture of dimethyl phthalate, allyl alcohol, and sodium ethoxide in benzene for 6–10 hours. At least about 0.15 wt. % of sodium is used in the process. U.S. Pat. No. 4,473,702 teaches to react dimethyl terephthalate with allyl alcohol in the presence of a two-component catalyst system that includes an organotin compound and another metal such as magnesium, aluminum, or zinc. In contrast, about 0.2 wt. % of sodium methoxide used with the organotin compound results in a slower reaction. U.S. Pat. No. 3,784,578 shows how to make DAP by reacting dimethyl phthalate with an excess of allyl acetate in the presence of potassium methoxide (0.1 to 10 wt. %). A subsequent distillation is required, however, to give a low-color product.

Japanese Pat. Appl. Kokai No. 5-25093 teaches to use at least about 0.1 wt. % of a composite catalyst of sodium methoxide and calcium hydroxide for transesterification of dimethyl phthalate with allyl alcohol. In addition, the reference teaches that using sodium methoxide alone gives unacceptably long reaction times and high product color.

Japanese Pat. Appl. Kokai No. 5-194324 teaches to use a composite catalyst of calcium hydroxide and an alkali metal salt of an organic or inorganic acid for the transesterification reaction to make DAP from dimethyl phthalate. The combined catalyst level is preferably 0.1 to 1.0 wt. %. Sodium methoxide alone gives a colored product when the process is used to make diallyl isophthalate.

An improved process for making allyl esters of aromatic carboxylic acids is needed. Preferably, the process would give fast reaction rates and high conversions to the desired allyl esters. Ideally, the process would use minimal levels of an inexpensive catalyst, simple techniques, and readily available equipment. A valuable process would give low-color products that do not require further distillation or treatment with an adsorbent to reduce color. A valuable process would use low enough catalyst levels to eliminate the need for water washing or neutralization to remove catalyst from the allyl ester product.

SUMMARY OF THE INVENTION

The invention is a transesterification process for making an allyl ester of an aromatic carboxylic acid. The process comprises first preparing a mixture of an alkyl ester of an aromatic carboxylic acid and an allylic alcohol. The mixture is distilled, optionally in the presence of an azeotroping solvent, to produce a dry mixture that contains less than about 200 ppm of water. The dry mixture is then heated in the presence of a transesterification catalyst, which is used in an amount effective to produce an allyl ester of the carboxylic acid. An alcohol by-product generated in the process is removed by distillation to give the purified allyl ester. The process is particularly useful for making diallyl phthalate from dialkyl esters of phthalic acid.

We surprisingly found that reducing the amount of water in alkyl ester-allylic alcohol mixtures to less than about 200 ppm is the key to improving process efficiency and product quality. With a dry reaction mixture, unexpectedly fast reaction rates and high conversions are obtained with a minimal level of transesterification catalyst. Low catalyst levels eliminate the need for water washing or neutralization to remove catalyst from the allyl ester. The process, which is simple to practice with conventional equipment, gives low-color allyl esters that require no further distillation or treatment with an adsorbent to reduce color.

DETAILED DESCRIPTION OF THE INVENTION

In the process of the invention, an alkyl ester of a carboxylic acid reacts with an allylic alcohol in the presence of a transesterification catalyst to produce an allyl ester of the aromatic carboxylic acid.

Suitable alkyl esters are derived from aromatic carboxylic acids. Aromatic carboxylic acids have one or more —COOH groups attached to an aromatic ring, e.g., a benzene ring. Preferred alkyl esters derive from the aromatic carboxylic acids and $C_1$–$C_6$ alcohols, and more preferably from $C_1$–$C_4$ alcohols such as methanol, ethanol, isopropyl alcohol, t-butyl alcohol, and the like. The aromatic carboxylic acid moiety preferably contains two or more carboxy groups. Suitable alkyl esters include, for example, methyl benzoate, dimethyl phthalate, diethyl phthalate, dimethyl isophthalate, diethyl terephthalate, di-t-butylphthalate, and the like, and mixtures thereof. Most preferred are dimethyl phthalate and diethyl phthalate.

An allylic alcohol is also used in the process. Suitable allylic alcohols have the general structure: $CH_2$=CR—$CH_2$—OH in which R is hydrogen or a $C_1$–$C_{10}$ aryl, alkyl, or aralkyl group. In preferred allylic alcohols, R is hydrogen or a $C_1$–$C_4$ alkyl group. Most preferred are allyl alcohol and methallyl alcohol.

The relative amounts of alkyl ester and allylic alcohol can vary over a fairly wide range. Usually, however, it is preferred to use at least one mole of allylic alcohol for every ester group equivalent. For example, when allyl alcohol reacts with dimethyl phthalate to produce diallyl phthalate, it is preferred to use at least about 2 moles of allyl alcohol per mole of dimethyl phthalate. In one preferred process of the invention, a substantial excess (typically 50 to 100%) of the allylic alcohol is used, and some of the allylic alcohol is removed in the distillation step for removing water to produce a dry mixture of the alkyl ester and allylic alcohol. In another preferred process, only a very slight excess of the allylic alcohol is used, but an azeotroping solvent (e.g., toluene) is included to assist in water removal.

The process of the invention is performed in the presence of a transesterification catalyst. Suitable transesterification catalysts are those commonly known in the art for ester interchange and alcoholysis reactions. These include, for example, alkali metal and alkaline earth metal alkoxides, Group III metal alkoxides, alkali metals, alkaline earth metals, organotin compounds, organotitanium compounds, metal oxides, and the like, and mixtures thereof. Examples of other suitable transesterification catalysts appear in U.S. Pat. Nos. 2,218,439, 3,784,578, and 4,473,702, the teachings of which are incorporated herein by reference. Preferred transesterification catalysts are alkali metal alkoxides such as sodium methoxide.

The amount of transesterification catalyst used in the process of the invention is important. We found that drying the reaction mixture well before introducing the catalyst greatly reduces the amount of catalyst needed for efficient transesterification. In prior-art methods, the amount of transesterification catalyst used is typically 0.1 to 10 wt. %. As the art teaches, the use of such large amounts of transesterification catalyst results in side reactions and unwanted color formation. Color removal often requires an added distillation step. In addition, catalyst removal by water washing or adsorption is necessary when such high catalyst levels are needed. The process of the invention enables greatly reduced catalyst levels and obviates these problems.

The actual amount of transesterification catalyst needed varies depending upon the nature of the catalyst, the nature of the alkyl ester and allylic alcohol used, the desired reaction time, and other factors. Preferably, however, the catalyst is used in an amount less than about 500 ppm based on the amount of alkyl ester used. A particularly preferred range for the catalyst is from about 10 to about 200 ppm; more preferred is the range from about 20 to about 100 ppm. At such low catalyst levels, color problems and the need for expensive catalyst removal procedures are often avoided.

The first step in the process of the invention involves preparing a mixture of the alkyl ester and allylic alcohol. These components are combined in any desired way, usually either at room temperature or elevated temperature. An azeotroping solvent can be included in the mixture.

The mixture is distilled to produce a dry mixture that contains less than about 200 ppm of water. Preferably, the dry mixture contains less than about 150 ppm of water; most preferred dry mixtures contain less than about 100 ppm of water. Thorough water removal enables faster transesterification reactions and the use of low catalyst levels. In practice, water is removed by distillation at or below atmospheric pressure. Generally, it is preferred to remove water by distilling from the reaction mixture a portion of the initially charged allylic alcohol. Water co-distills with the allylic alcohol until less than about 200 ppm water remains. When this procedure is used, an amount of the allylic alcohol in excess of the amount required stoichiometrically for ester formation, i.e., a substantial excess, is initially charged to the reactor. Another approach includes an azeotroping solvent such as toluene to assist in water removal. When an azeotroping solvent is used, only a slight excess of the allylic alcohol is necessary.

After the mixture is sufficiently dry, the transesterification catalyst is added and the mixture is heated. Usually, the mixture is heated under reflux in a manner effective to allow alcohol by-products derived from the alkyl ester to be removed by distillation. The allyl ester product and starting materials (allylic alcohol, alkyl ester, and catalyst) remain in the reactor. Removal of alcohol by-products drives the reaction toward complete conversion to the desired allyl ester. While any desired reaction temperature can be used, it is generally preferred to perform the transesterification reaction at a temperature within the range of about 60° C. to about 200° C. A more preferred range is from about 80° C. to about 150° C.

The transesterification catalyst can be added in a single portion following combination of the alkyl ester and allylic alcohol. Alternatively, the catalyst can be added incrementally or continuously to the heated reaction mixture. Either way, the catalyst can be added in solid or neat liquid form or as a dilute solution. Using a dilute solution of the catalyst (e.g., sodium methoxide in methanol, less than 10 wt. %, preferably less than 5 wt. %) offers the advantage of allyl esters with exceptionally low color. Adding the catalyst in increments promotes a consistently high and steady reaction rate throughout the transesterification, and balances the tendency of some catalysts to deactivate as the reaction proceeds. Even when the catalyst is added incrementally, very low total catalyst levels (less than 200 ppm) are effective (see Table 2).

The process of the invention includes batch, semi-batch, and continuous processes. In a typical batch process, the reactants (except for the catalyst) are charged to a reactor, the mixture is heated under reflux, water and allylic alcohol (and/or azeotroping solvent) are removed, catalyst is introduced, the mixture is heated to promote transesterification, and alcohol by-products are removed by distillation. The allyl ester can be recovered as a bottom product following removal by distillation of any unreacted allylic alcohol and simple filtration. In a typical continuous process, streams of the allylic alcohol, alkyl ester, and transesterification catalyst are fed continuously into a heated reaction zone, and the allyl ester, alcohol by-products, and catalyst are continuously separated downstream from the reaction zone.

The process of the invention offers valuable and unexpected advantages. First, drying the mixture to less than about 200 ppm water content enables transesterification at exceptionally low catalyst levels (100 ppm and less based on the amount of alkyl ester) compared with the levels described in the prior art (typically 1000 ppm or more). Thus, catalyst costs are reduced. Second, the reaction is complete in as little as a few hours even at low catalyst levels, so productivity improves. Third, the process gives allyl esters that have low color (typically less than about 100 APHA, and often less than about 30 APHA), so subsequent treatments to reduce color are avoided. Product color can be further reduced, if desired, by treating the crude allyl ester with an adsorbent such as magnesium silicate, although this is usually not necessary. The ability to further reduce color by adsorbent treatment overcomes the need to use a more difficult and expensive distillation procedure. Fourth, the allyl ester product, after stripping of unreacted allylic alcohol and simple filtration to remove solids, usually meets all product specifications. Subsequent distillation of the allyl ester to reduce color or remove contaminants is usually not needed. In addition, the process avoids any need for water washing or treatment with an adsorbent (such as magnesium silicate) to remove residual catalyst. This contrasts with conventional processes that usually require distillation of the allyl ester to reduce color, and water washing and/or adsorbent treatment to remove catalyst residues.

The following examples merely illustrate the invention. Those skilled in the art will recognize many variations that are within the spirit of the invention and scope of the claims.

EXAMPLES 1–3 and COMPARATIVE EXAMPLES 4–6

Preparation of Diallyl Phthalate from Dimethyl Phthalate: Effect of Water Content and Catalyst Level on Percent Conversion A two-liter reaction flask equipped with heating mantle, thermocouples, packed column, reflux condenser, reflux splitter, overhead receiver, and inlets for nitrogen and vacuum is charged with dimethyl phthalate (200 g) and allyl alcohol (200 g). The mixture is dried by distilling allyl alcohol and water overhead until the pot mixture has the desired water concentration (see Table 1). The actual water content is determined by Karl Fischer titration. The column is then switched to total reflux, and sodium methoxide (amount shown in Table 1) is added to the flask. The reflux ratio is adjusted to distill off pure methanol. Percent conversion of dimethyl phthalate (see Table 1) is determined by measuring the amount of methanol collected.

As Comparative Example 4 shows, the reaction is slow even with a very dry mixture at 10 ppm catalyst. Comparative Examples 5 and 6 show that little or no conversion occurs even at 30 ppm catalyst if the water content of the mixture is 180 ppm or more. Surprisingly, however, significant conversion results, even at only 30 ppm catalyst, when the water content of the reaction mixture is 120 ppm or less. In addition, the percent conversion is directly related to how dry the reaction mixture is; the drier the reaction mixture, the higher the percent conversion at 30 ppm catalyst.

EXAMPLE 7

Preparation of Diallyl Phthalate from Dimethyl Phthalate

Dimethyl phthalate (291 g) and allyl alcohol (290 g) are charged to a two-liter reactor equipped as described above. The mixture is dried by distilling about 10.6 g of allyl alcohol/water mixture from the flask. Allyl alcohol (104 g) is mixed with methanolic sodium methoxide (0.48 g of 25 wt. % NaOCH$_3$ in methanol) to give a 0.115 wt. % solution of sodium methoxide in methanol/allyl alcohol ("catalyst solution"). The column is set for total reflux, and some of the catalyst solution (20 mL; equivalent to 35 ppm sodium methoxide) is added to the flask. Methanol is removed overhead by distillation until the reaction is complete. Additional catalyst solution (20 mL increments) is added after 2 and 3 hours of reaction time for a total about 100 ppm sodium methoxide. After 4.75 h, the remaining allyl alcohol is removed by vacuum stripping, leaving 360 g of product. Gas chromatography analysis reveals 99.5% of diallyl phthalate, 0.2 wt. % of methyl allyl phthalate, and no detectable dimethyl phthalate.

This example demonstrates that excellent conversions (>99%) can be achieved in short reaction times (<5 h) at very low catalyst concentrations (100 ppm) if the reaction mixture is dried to a water content of less than 200 ppm before performing the transesterification reaction.

EXAMPLES 8–10 and COMPARATIVE EXAMPLES 11–13

Effect of Catalyst Concentration on Product Color

Using the equipment previously described, a mixture of allyl alcohol and dimethyl phthalate containing a 60–100% excess of allyl alcohol is charged to the reactor. The mixture is dried by distilling allyl alcohol/water mixture overhead until the reaction flask contains less than 200 ppm of water. An initial catalyst charge (see Table 2) is added to the flask. Additional catalyst is added to the reactor whenever the methanol take-off rate diminishes. Reaction proceeds until no further methanol distills. Excess allyl alcohol is removed by vacuum stripping, and the APHA color of the product is measured (see Table 2).

As Table 2 shows, catalyst concentrations commonly reported in the art (600–3400 ppm) give diallyl phthalate products with unacceptably high color (APHA>150, see Comparative Examples 11–13) even at low water contents. A typical color specification for diallyl phthalate is less than APHA 100, preferably less than APHA 70. The results are consistent with teachings in the art about color formation with sodium methoxide. However, as Examples 8–10 show, the use of very low catalyst levels (55 to 104 ppm), combined with low water content (<200 ppm) results in both high conversion (99%) and low color (APHA 30 to 100).

The preceding examples are meant only as illustrations; the following claims define the scope of the invention.

TABLE 1

Effect of Water Content and Catalyst Concentration on % Conversion: Preparation of Diallyl Phthalate from Dimethyl Phthalate

| Ex. # | Water (ppm) | NaOCH$_3$ (ppm) | % Conversion |
|---|---|---|---|
| 1 | <60 | 30 | 84 |
| 2 | 85 | 30 | 50 |
| 3 | 120 | 30 | 22 |
| C4 | <60 | 10 | ~0 |
| C5 | 180 | 30 | ~0 |
| C6 | 215 | 30 | ~0 |

C—denotes comparative examples

TABLE 2

Effect of Catalyst Concentration on Product Color: Preparation of Diallyl Phthalate from Dimethyl Phthalate

| Ex. # | Initial NaOCH$_3$ concentration (ppm) | Total NaOCH$_3$ concentration (ppm) | Conversion (%) | APHA Color |
|---|---|---|---|---|
| 8 | 22 | 55 | 99 | 30 |
| 9 | 23 | 92 | 99 | 40 |
| 10 | 26 | 104 | 99 | 100 |
| C11 | 200 | 600 | 98 | >150 (yellow) |
| C12 | 200 | 800 | 98 | >150 (yellow) |
| C13 | 3400 | 3400 | 95 | >>150 (dark orange) |

C—denotes comparative examples

We claim:

1. A transesterification process for making an allyl ester of an aromatic carboxylic acid, said process comprising:
   (a) preparing a mixture of an alkyl ester of an aromatic carboxylic acid and an allylic alcohol;
   (b) distilling the mixture to produce a dry mixture that contains less than about 200 ppm of water;
   (c) heating the dry mixture in the presence of an amount of a transesterification catalyst effective to produce an allyl ester of the carboxylic acid and an alcohol by-product;
   (d) distilling alcohol by-product from the mixture to produce a purified allyl ester of the carboxylic acid.

2. The process of claim 1 wherein the allylic alcohol is allyl alcohol, the alkyl ester is dimethyl phthalate or diethyl phthalate, and the allyl ester is diallyl phthalate.

3. The process of claim 1 wherein the transesterification catalyst is an alkali metal alkoxide selected from the group consisting of sodium methoxide and potassium methoxide.

4. The process of claim 1 wherein the transesterification catalyst is added incrementally to the heated reaction mixture.

5. The process of claim 1 wherein the total amount of transesterification catalyst used is less than about 500 ppm based on the amount of alkyl ester.

6. The process of claim 1 wherein the transesterification catalyst is sodium methoxide, and the total amount of sodium methoxide used is within the range of about 10 to about 200 ppm based on the amount of alkyl ester.

7. The process of claim 2 wherein the resulting diallyl phthalate has an APHA color less than or equal to about 100.

8. A transesterification process for making diallyl phthalate, said process comprising:
   (a) preparing a mixture of an ester selected from the group consisting of dimethyl phthalate and diethyl phthalate, and allyl alcohol;
   (b) distilling the mixture to produce a dry mixture that contains less than about 150 ppm of water;
   (c) heating the dry mixture in the presence of an amount of an alkali metal alkoxide catalyst effective to produce diallyl phthalate and methanol or ethanol;
   (d) distilling methanol or ethanol from the mixture to produce purified diallyl phthalate.

9. The process of claim 8 wherein the alkali metal alkoxide catalyst is selected from the group consisting of sodium methoxide and potassium methoxide.

10. The process of claim 8 wherein the alkali metal alkoxide catalyst is added incrementally to the heated reaction mixture.

11. The process of claim 8 wherein the total amount of alkali metal alkoxide catalyst used is less than about 500 ppm based on the amount of dimethyl or diethyl phthalate.

12. The process of claim 8 wherein the alkali metal alkoxide catalyst is sodium methoxide, and the total amount of sodium methoxide used is within the range of about 10 to about 200 ppm based on the amount of dimethyl or diethyl phthalate.

13. The process of claim 8 wherein the diallyl phthalate has an APHA color less than or equal to about 100.

* * * * *